US006288393B1

(12) United States Patent
Phaneuf et al.

(10) Patent No.: US 6,288,393 B1
(45) Date of Patent: *Sep. 11, 2001

(54) AUTOMATED METHOD OF CIRCUIT ANALYSIS

(75) Inventors: Michael Phaneuf, Ottawa; Dick James, Carp; Pierrette Breton, Stittsville; Julia Elvidge, Ottawa; Ray Haythornthwaite, Nepean, all of (CA)

(73) Assignee: Chipworks, Ottawa (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/238,436

(22) Filed: Jan. 28, 1999

Related U.S. Application Data

(60) Provisional application No. 60/072,873, filed on Jan. 28, 1998.

(51) Int. Cl.[7] .................................................. G01N 23/225
(52) U.S. Cl. ............................................. 250/307; 250/309
(58) Field of Search ................................ 250/307, 491.1, 250/309, 492.2

(56) References Cited

U.S. PATENT DOCUMENTS

| | | | |
|---|---|---|---|
| 4,553,260 | 11/1985 | Belt et al. ............................... | 382/22 |
| 4,623,255 | 11/1986 | Suszko .................................. | 356/389 |
| 4,639,301 | 1/1987 | Doherty et al. ................. | 204/192.31 |
| 4,673,101 | 6/1987 | Guarino et al. ...................... | 220/335 |
| 4,698,236 | * 10/1987 | Kellogg et al. .................... | 250/492.2 |
| 4,699,555 | 10/1987 | Guarino ................................ | 414/217 |
| 4,711,438 | 12/1987 | Guarino ................................ | 269/152 |
| 4,748,675 | 5/1988 | Suzuki et al. ........................ | 382/21 |
| 4,766,516 | 8/1988 | Ozdemir et al. ..................... | 361/380 |
| 4,777,372 | 10/1988 | Guarino ............................. | 250/442.1 |
| 4,783,829 | 11/1988 | Miyakawa et al. ..................... | 382/22 |
| 4,791,586 | 12/1988 | Maeda et al. ......................... | 364/491 |
| 4,874,947 | 10/1989 | Ward et al. ........................... | 250/309 |
| 4,943,732 | 7/1990 | Economou ............................ | 250/572 |
| 4,976,843 | 12/1990 | Ward et al. ....................... | 204/298.36 |
| 5,008,537 | * 4/1991 | Toita et al. ............................ | 250/309 |
| 5,034,612 | 7/1991 | Ward et al. ....................... | 250/423 R |
| 5,050,222 | 9/1991 | Lee ......................................... | 382/21 |
| 5,086,477 | 2/1992 | Yu et al. ................................. | 382/8 |
| 5,103,102 | 4/1992 | Economou et al. .............. | 250/492.2 |

(List continued on next page.)

FOREIGN PATENT DOCUMENTS

| | | | | |
|---|---|---|---|---|
| 2168328 | 1/1996 | (CA) | ................................ | G06T/7/60 |
| 2216900 | 9/1997 | (CA) | ................................ | G06T/7/60 |

OTHER PUBLICATIONS

Welcome to Philips Electroscan, http://www.electroscan.com/.

"Ion Beams in Focus," European Semiconductor, Mar. 1996, pp. 49–50.

T.O. Kiang and E.M. Hwa, "Extracting Layers from Optical Images of Silicon Integrated Circuit Chips," pp. 571–575.

O.K. Tan, M.H. Er, Y.W. Chow, W.S. Chow, "An Automatic Layer Extractor of IC Chips," pp. 1346–1349.

(List continued on next page.)

*Primary Examiner*—Jack Berman
(74) *Attorney, Agent, or Firm*—Freedman & Associates

(57) ABSTRACT

A method of analysing integrated circuits is provided. The method provides for scanning the integrated circuit with a beam in order to image an upper layer of the integrated circuit and performing chemical analysis on the upper layer of the integrated circuit. The chemical information and the imaging information are correlated and used to reverse engineer the integrated circuit.

13 Claims, 4 Drawing Sheets

U.S. PATENT DOCUMENTS

| | | | |
|---|---|---|---|
| 5,118,941 | * 6/1992 | Larson | 250/307 |
| 5,155,368 | 10/1992 | Edwards, Jr. et al. | 250/396 R |
| 5,163,005 | 11/1992 | Greene et al. | 364/468 |
| 5,187,754 | 2/1993 | Currin et al. | 382/54 |
| 5,188,705 | 2/1993 | Swanson et al. | 156/643 |
| 5,191,213 | 3/1993 | Ahmed et al. | 250/310 |
| 5,199,159 | 4/1993 | Waldsmith | 29/596 |
| 5,214,718 | 5/1993 | Khosla | 382/22 |
| 5,241,182 | 8/1993 | Martin et al. | 250/396 R |
| 5,329,162 | 7/1994 | Nadaoka | 257/774 |
| 5,335,298 | 8/1994 | Hevenor et al. | 382/54 |
| 5,376,791 | 12/1994 | Swanson et al. | 250/309 |
| 5,392,222 | 2/1995 | Noble | 364/490 |
| 5,399,441 | 3/1995 | Bearinger et al. | 428/689 |
| 5,435,850 | 7/1995 | Rasmussen | 118/726 |
| 5,502,306 | 3/1996 | Meisburger et al. | 250/310 |
| 5,541,411 | 7/1996 | Lindquist et al. | 250/309 |
| 5,559,718 | 9/1996 | Baisuck et al. | 364/491 |
| 5,561,293 | 10/1996 | Peng et al. | 250/307 |
| 5,578,821 | 11/1996 | Meisberger et al. | 250/310 |
| 5,616,921 | * 4/1997 | Talbot et al. | 250/307 |
| 5,694,481 | 12/1997 | Lam et al. | 382/145 |
| 5,821,549 | * 10/1998 | Talbot et al. | 250/307 |

OTHER PUBLICATIONS

C.C. Jong, O.K. Tan, S.C. Sing., M.L.J.Siow, "Geometrical figure processing for IC layout extracted from silicon die image," Int. J. Electronics, 1995, vol. 78, No. 2, pp. 367–394.

Jong et al. "Computer–aided Reconstruction of IC Layout from Image–based representation" Proceedings of the $5^{th}$ International Symposium on IC Technology System and Applications pp. 466–469, Sep. 1993.

Tan et al. "Integrated Circuit Chip Layer Analysis" Proceedings of the $5^{th}$ International Symposium on IC Technology System and Applications pp. 461–465, Sep. 1993.

* cited by examiner

AUTOMATED METHOD OF CIRCUIT ANALYSIS

This Application claims benefit to Provisional Application No. 60/072,873 filed Jan. 28, 1998.

FIELD OF THE INVENTION

The invention relates to integrated circuit imaging and analysis and more particularly to the use of an imaging system and a chemical analysis system for reverse engineering layers of integrated circuits.

BACKGROUND OF THE INVENTION

In the past, reverse engineering of circuits was a straight-forward task. A circuit board was examined for traces providing a series of conductive connections between components. Circuit components were then analysed to determine connected elements and finally, a schematic of the board was entered for improvement, re-layout, or incorporation into a current design.

With the advent of MSI, LSI, and VLSI, this process became far more tedious. Initial attempts at reverse engineering integrated circuits relied on visual images of integrated circuit layers. Overlapping portions of a layer of an integrated circuit were photographed such that a portion of the layer is photographed. The images were developed as photographs and the photographs were assembled by hand in order to overlap adjacent images appropriately. Because of the redundant nature of integrated circuits, assembling the overlapping images into a single large composite image was difficult and required some skill.

Once a composite image was formed by taping or gluing the photographs together in an appropriate fashion, analysis of the images began. The analysis was performed by a skilled person in the art of reverse engineering or integrated circuit fault analysis who performed the steps of determining conductors, transistors, capacitors, resistors, etc. and forming a schematic of the circuit in dependence upon the analysis. Unfortunately, similarities of colour, contrast, and other output data provided by imaging systems used in reverse engineering, are often not determinative of similarity of material(s).

Reverse engineering a complex integrated circuit often represents several man months of effort and requires significant contribution by highly skilled individuals. Extraction of information requires skilled individuals to analyse images of layers and identify regions of particular materials based on experience and deduction. In essence, skilled individuals reconstruct layout information. Even though this approach is currently acceptable, it is very costly due to the time and effort required. For example, a single integrated circuit may comprise 10,000 images for a single layer. To analyse and infer information for each image is a very time consuming process.

It would be advantageous to automate some of the functions required to reverse engineer or analyse layers within an integrated circuit (IC).

PRIOR ART

In U.S. Pat. No. 4,623,255 in the name of Suszko and issued on Nov. 18, 1986, a Method of Examining Microcircuit Patterns is disclosed. The method comprises the steps of photographing a portion of an IC with dark field illumination and then developing the photograph. As described above, the mosaic formed by assembling photographs is time consuming and requires significant expertise.

In U.S. Pat. No. 5,086,477 in the name of Yu et al. and issued on Feb. 4, 1992, an Automated System for Extracting Design and Layout Information from an Integrated Circuit is disclosed. The system comprises an image capture means for capturing a plurality of images of an IC and a computer for assembling the images into a large mosaic by determining image overlap or by extrapolating images to fill gaps between adjacent images. Unfortunately, when working with current IC tolerances, gaps between abutting images may contain important circuit elements. Further the system taught by Yu et al. requires a known element to occur on each of several layers in order to align image composites for a multi-layer IC. The known element is identified by a skilled worker. Finding and identifying such an element on each layer of the IC is often time consuming. Also, removing an IC from the imaging system in order to prepare it for imaging successive layers, makes aligning successive layers automatically very difficult.

In U.S. Pat. No. 5,191,213 in the name of Ahmed et al. and issued on Mar. 2, 1993, an Integrated Circuit Structure Analysis method and apparatus are disclosed. An electron beam is directed toward successive layers of an IC. Some known problems with the use of electron beam scanning of IC layers are solved by Ahmed et al. but, reverse engineering of IC layers is not easily performed. Also, removing an IC from the imaging system in order to prepare it for imaging successive layers makes aligning successive layers in an automatic fashion very difficult.

In U.S. Pat. No. 5,694,481 in the name of Lam et al. and issued Dec. 2, 1997, a system for automatically constructing a mosaic of images using polygon extraction and filtering of images is disclosed. The method appears useful for imaging circuit information from SEM image data. The method disclosed presents no information on extracting chemical/circuit related information from the imaged IC. Unfortunately, a skilled individual using inference must perform further analysis of the layers. As such, the analysis is time consuming.

Scanning electron microscope (SEM) systems are known for use in imaging of integrated circuits. Using an SEM system, a beam of electrons is directed toward a surface to be imaged and scattered electrons from the surface are detected and analysed. The resulting information is used to determine an image. Because electrons are very small and beam energies are notable, electrons penetrate the surface and the image information that results is of the surface and details below the surface.

Focused ion beam (FIB) systems are known for use in several applications. FIB systems are useful in micromachining, imaging and etching. The use of FIB systems in imaging is well documented. In imaging, an ion beam is focused toward a location and backscattered ions are detected. Other particle emissions caused by collisions between ions within the beam and a surface being imaged may also be detected. Analysis of the detected particles results in an image. FIB systems are also used in etching. Etching with FIB systems began with applications for cutting traces in integrated circuits to allow for IC repair. With gas assisted etching, FIB systems provide a convenient system for etching away selected material from a surface of an IC in order to form holes of a desired depth.

Gas assisted etching is performed as follows. A reactive gas such as chlorine is fed into the FIB system near a surface of a substrate. The gas adsorbs to the surface approximating a monolayer. When the surface is scanned with ion beams, the energy of the ion beams is used to break chemical bonds, thus causing chemical reactions to proceed. As well as providing the energy needed to break bonds, the ions supply momentum to sputter the substrate. The chemical etching helps to enhance the physical sputtering of the ion beam. Another benefit is that the sputtered particles are volatilised and pumped away by a vacuum system forming part of the FIB systems.

Use of correct etchant gas significantly increases etching rate over FIB etching without an etchant gas. The increased etching rate is material dependent so selection of a gas for a particular material results in improved etching performance and improved control because of etching rate decreases when different material is exposed. These two advantages to gas assisted etching are known to allow etching of deep narrow holes.

Using a FIB system or a SEM system, information results in the form of images. These images, distinguish between different results using colour or intensity. FIB systems are particularly good for distinguishing between certain types of materials. Similarly, SEM systems are good at distinguishing certain types of materials. Some materials, though very different in nature, appear very similar in the images formed.

It would be advantageous to provide a method of imaging a layer within an integrated circuit to extract geometric information relating to regions within the layer wherein the information is based on the chemical composition of the materials.

SUMMARY OF THE INVENTION

In accordance with the invention there is provided a method of analysing an integrated circuit comprising the steps of:

disposing the integrated circuit on a support for securing the integrated circuit in a fixed relation to the support; and iterating the following steps until a predetermined portion of an integrated circuit is imaged:

using an imaging system for providing a beam relatively movable to said support, imaging a portion of an outer surface of the integrated circuit by capturing a plurality of images of different locations on the integrated circuit, relative motion between the support and the beam occurring between image capture operations;

analysing chemical composition of a portion of the outer surface of the integrated circuit using a chemical analysis system relatively movable to said support; and, analysing the plurality of captured images with a processor, the analysis performed in dependence upon the analysed chemical information.

In accordance with the invention, there is provided a method of analysing an integrated circuit comprising the steps of:

disposing the integrated circuit on a support for securing the integrated circuit in a fixed relation to the support; and iterating the following steps until a predetermined portion of an integrated circuit is imaged:

using an imaging system for providing a beam relatively movable to said support, imaging a portion of an outer surface of the integrated circuit by capturing a plurality of images of different locations on the integrated circuit, relative motion between the support and the beam occurring between image capture operations;

using a chemical analysis system, analysing chemical composition of a portion of the outer surface of the integrated circuit; and, analysing the plurality of captured images with a processor, by associating analysed chemical information and intensity values of pixels within the images at a same location as a location of the analysed chemical information, the analysis performed in dependence upon the intensity values and associated chemical information.

In accordance with the invention there is provided a method of analysing an integrated circuit comprising the steps of:

disposing the integrated circuit on a support for securing the integrated circuit in a fixed relation to the support; and iterating the following steps until a predetermined portion of an integrated circuit is imaged:

using an imaging system including a focused ion beam imaging device and a SIMS chemical analysis device relatively movable to said support, imaging a portion of an outer surface of the integrated circuit by capturing a plurality of images of different locations on the integrated circuit with the imaging device and simultaneously analysing chemical information of the different locations using the SIMS device, relative motion between the support and the imaging system occurring between image capture operations; and analysing the plurality of captured images with a processor, the analysis performed in dependence upon the analysed chemical information.

In an embodiment, the IC is marked with alignment marks. For example, an SEM system disposes carbon on the IC for marking it. Alternatively, an FIB system etches marks into the IC.

Advantageously, a method according to the present invention allows for imaging of regions within a doped layer of an integrated circuit in order to extract accurate material and area geometry information.

BRIEF DESCRIPTION OF THE DRAWINGS

An exemplary embodiment of the invention will now be discussed in conjunction with the attached drawings in which.

DETAILED DESCRIPTION OF THE INVENTION

Examining and understanding integrated circuits (ICs) has numerous applications. Designers often review integrated circuit components of competitive manufacturers in order to improve their designs; in patent infringement actions, an explanation of an IC's circuitry and mode of operation is sometimes required; and, in reverse engineering—copying functionality—of an integrated circuit component, months can be eliminated from a design cycle. Current practices, though often significantly faster than an entire engineering redesign, are tedious and require significant levels of skill.

Figure 1:
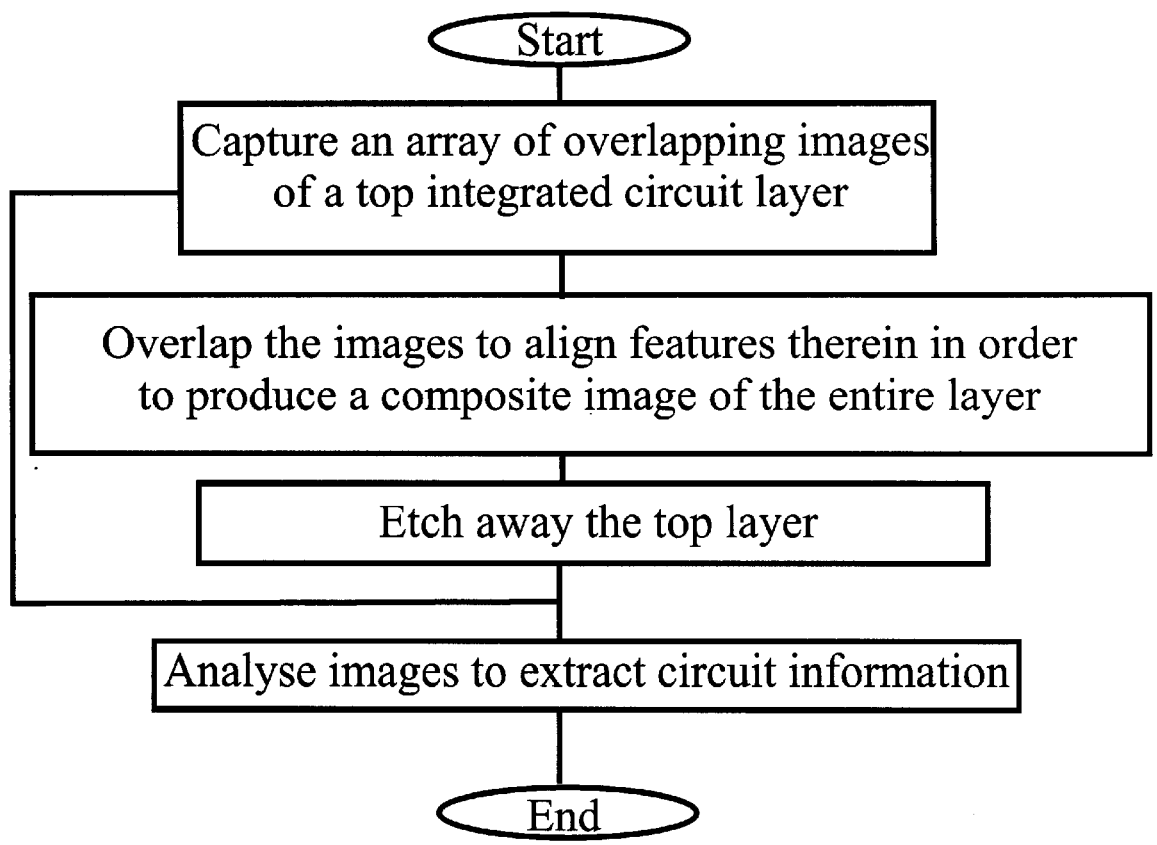
FIG. 1 is a simplified flow diagram of a method according to the prior art of imaging an IC using mosaicing.

Referring to FIG. 1, a simplified block diagram of prior art reverse engineering processes is shown. An imager is used to image a layer of an IC. Unfortunately, because of the detail contained in a single IC layer, the imager is capable of imaging only a small section of a layer at a time. Further, due to the spacing of traces within an IC, imaging systems can not image abutting images accurately. Therefore, a stage is provided for moving the IC relative to the imager. A plurality of images is captured in order to ensure that the entire area of a desired portion of the IC layer is imaged.

The images are then assembled at an assembly station. An assembly station often comprises a large table where the images are laid out and aligned by hand. Alternatively, current trends toward computer aided design propose that a computer algorithm be used to align images and mosaic them into a single final composite image of a layer. The composite image is then stored for further analysis. Unfortunately, due to the large amount of redundancy in a typical IC and the limited information contained within each image frame, automatic alignment of images is very difficult and a detailed review of the images and their alignment is necessary prior to analysing the composite image formed.

Once a layer is imaged, the IC is removed from the imaging station and moved to an etching station. At the etching station, a layer of material is removed from the IC to expose another layer of circuitry. The IC is then returned to the imaging station for imaging of this other layer. Since current IC tolerances are less than a micron, it is near impossible to ensure accurate placement and alignment of the IC with each insertion into the imaging station. Therefore, a composite image alignment station is required. At the composite image alignment station, the composite images are stacked together and features on adjacent layers are identified by hand in order to determine inter layer connections and inter layer alignment.

The resulting three-dimensional composite image is analysed to determine a schematic or other representation of the circuitry. During an analysis stage, experienced individuals identify circuit components and deduce chemical composition of those components, when necessary. This allows for entry of a schematic and/or layout of the integrated circuit for manufacture or simulation.

Because the analysis of circuit information is partially inferential, it is expensive and prone to error. It would be beneficial to provide an automated circuit analysis system.

As is evident to those of skill in the art, the above-described method requires days or weeks of effort. The imaging and etching process requires significant human intervention and the resulting data requires a significant amount of human assisted interpretation. The chemical information extracted is often a result of inference—educated guesses—by an experienced individual.

As traces on integrated circuits are made smaller, the limitations of optical imaging using conventional microscopes are apparent. Current integrated circuit spacing is generally sufficiently large for optical imaging; this will likely be untrue in a few years.

Throughout the specification and the claims the term capturing an image or captured image refers to individual images captured by an image capture means. The term imaging is used in its general meaning and is not limited to optical imaging. Also, the term pixel is used to refer to a single imaged point or location. Such a point represents a quantisation of a two dimensional view. For example, a pixel may represent a circular region 0.1 micron in diameter.

Figure 2:
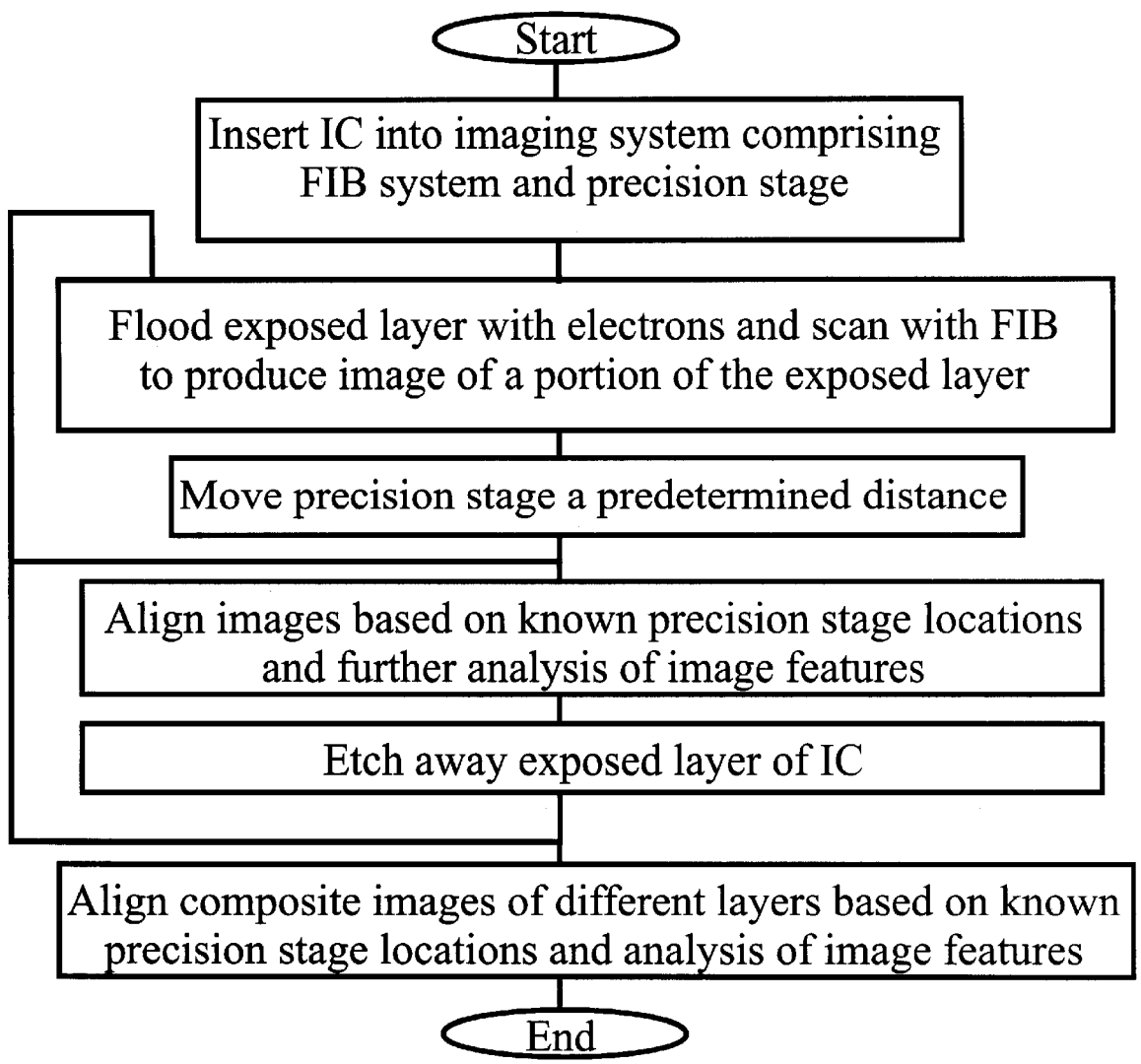
FIG. 2 is a simplified flow diagram of a method according to the invention of imaging an IC using a FIB and chemical analysis information.

Referring to FIG. 2, a simplified flow diagram of a method according to the present invention is shown. An IC is inserted onto a precision stage for imaging by a beam imaging device. The following disclosure pertains to the use of a focused ion beam (FIB) imaging device and a secondary ion mass spectrometer (SIMS). Alternatively, a scanning electron microscope (SEM) beam imaging system and/or another chemical analysis system is used.

Using a FIB imaging system, gallium ions are projected toward the IC surface. Upon impinging on the IC surface, both electrons and ions are sputtered. Some of these sputtered particles are analysed in order to generate an image of the IC. In general, ions sputtered from the surface provide relatively accurate spatial location information. This accuracy is enhanced by rendering electrical charge on the surface of the IC uniform. A known method of accomplishing this is by flooding the surface with low energy electrons. Of course, when sputtered electrons are to be analysed, flooding the surface with low energy electrons is not performed.

Preferably, the IC is prepared, having a first layer exposed for imaging. The IC is secured in place by securing means. Securing means for retaining ICs in place during imaging are well known and include the use of adhesives, mechanical clamping, etc.

A surface of an exposed layer for imaging is flooded with a low energy electron flow. As described above, these electrons help neutralise charge on insulated portions of the circuit and, thereby, improve image accuracy and alignment. The FIB imaging device captures an image of a portion of the IC layer.

Alternating with FIB imaging, a secondary ion mass spectrometer (SIMS) system is used to analyse chemical information of the IC. For example, portions within the FIB image are identified through image analysis, pixels corresponding to those portions having similar but different values. SIMS analysis enables a determination of chemical compositions that are likely indicated by particular pixel values. Of course, when desired an entire portion of the IC is analysed using the SIMS device.

The SIMS data is likely to contain some gallium implanted by the FIB during imaging. Therefore, when gallium is a significant element within an IC, a different imaging method such as SEM is used or, alternatively, SEM and FIB imaging devices are both used, the SEM imaging device before the chemical analysis is performed and the FIB imaging system after the chemical analysis is performed. An example of a suitable chemical analysis system is Energy Dispersive X-Ray (EDX) spectroscopy.

A precision stage upon which the IC is mounted is used to permit chemical analysis of portions of an image that, through analysis, are selected for chemical analysis. Once the chemical analysis and imaging of a portion of the IC is completed, the precision stage is moved to allow capturing of an image of another portion of the integrated circuit. Preferably, stage precision is at least as accurate as minimal spacing within an IC. The use of an interferometric precision stage as is available in currently available FIB systems allows for such precision. Preferably, captured images overlap a predetermined amount in order to provide a confirmation of stage accuracy. Further images of portions of the IC layer are captured until a mosaic of the entire layer can be constructed from the captured image data.

When a stage is accurate, image overlap is obviated and image alignment is known. Unfortunately, due to the precision of current ICs, a precision of better than 0.1 microns is required of an accurate stage in order to allow straightforward alignment based on stage positioning and image processing. Because of the redundant nature of integrated circuits, precision of better than ⅓ of trace spacing is required in order to provide a truly indicative estimate of alignment. Image processing is then capable of deterministically aligning the images. As is evident to those of skill in the art, at current rates of progress a stage having a precision of 0.1 microns is unlikely to remain sufficiently precise for a significant length of time. Because of this, it is advantageous to improve methods of processor based image alignment in order to maintain current functionality with denser ICs without replacing an entire imaging system or precision stage.

The FIB imaging apparatus is used to etch away material from the exposed IC layer in a selective fashion. This allows for imaging of subsequent layers in an automated fashion without requiring removal and replacement of the IC. Of course, using the FIB imaging system for etching results in significant implantation of gallium ions and is therefore well suited to applications where gallium is known to be absent from an integrated circuit.

For metal layers, this is a convenient method of ensuring alignment between layers. Using a precision stage, alignment between layers is known within the precision of the stage, because the IC has not been moved. Further, by etching only a portion of the exposed layer, accurate alignment between layers is ensured using a simple image correlation technique whether or not a precision stage is used.

Once imaging of portions of the IC is complete, the images and the chemical information are used to determine circuit and layout information for the circuit. For example, a list of substances that are usually conductors such as aluminium, tungsten, gold, silver, copper and so forth is maintained. When chemical information indicates a conductor, those areas of the image(s) that correspond to the analysed chemical information are determined to be conductors. Several advantages to this approach exist. Firstly, different substances such as aluminium and tungsten are used as conductors within a single IC. That said, each has a specific purpose and identification of interconnect materials helps identify purpose and further interconnections. Areas within the images having similar pixel values are assumed to be a similar material, but further analysis is performed to verify this assumption or to reject it.

Also, providing chemical information allows for additional verification of mosaicing. For example, similar substances near adjacent edges of adjacent image frames align when overlap between images exists and, align most often even when no overlap between images exists. Also, analysis of chemical information eliminates some of the guesswork from reverse engineering. This allows a less experienced individual to perform many reverse-engineering functions.

Figure 3:
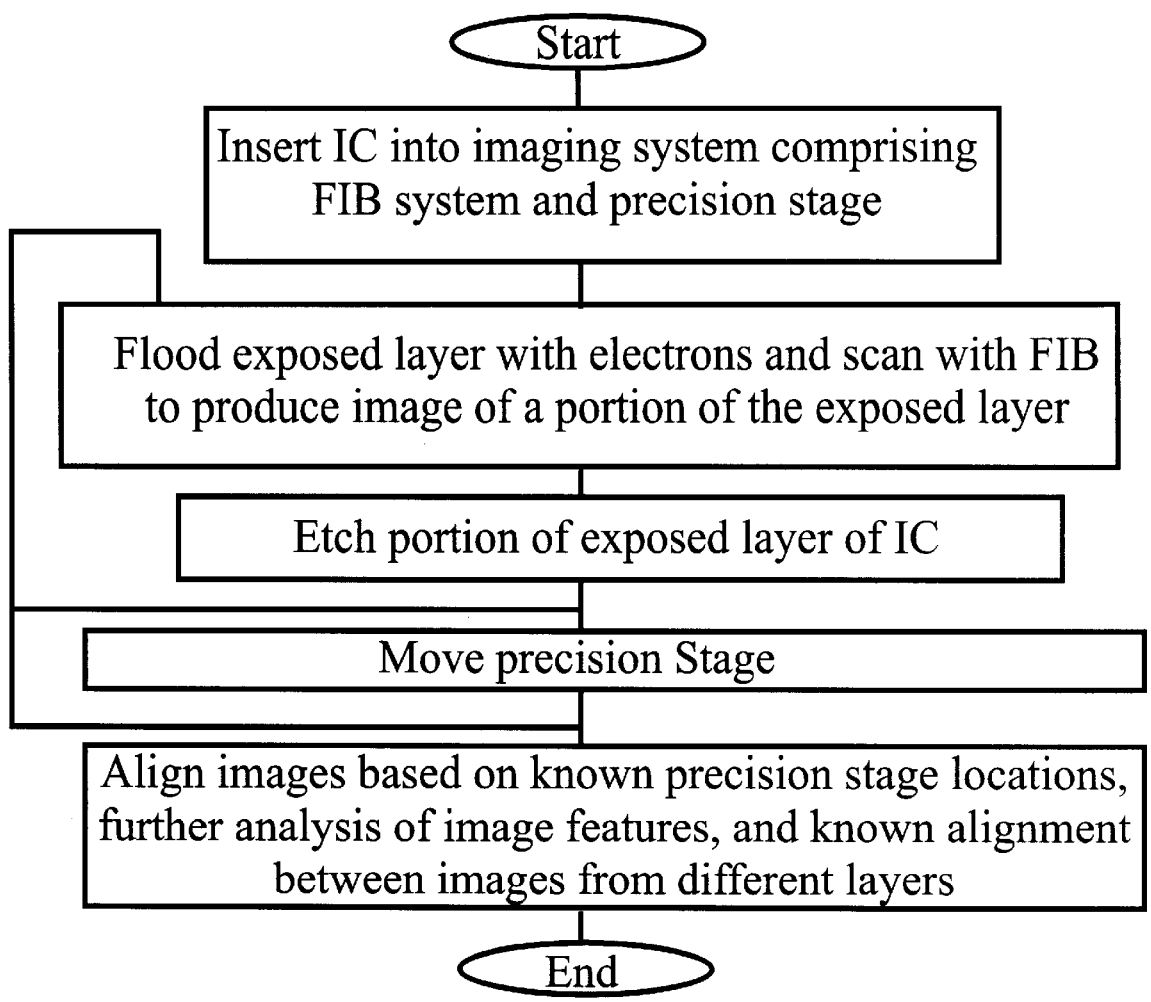
FIG. 3 is a simplified flow diagram of a method according to the invention of imaging an IC using a SEM and chemical analysis information; and, FIG. 4 is a simplified flow diagram of a method of imaging a doped layer of an integrated circuit according to the invention.

Referring to FIG. 3, a method of imaging a layer of an IC according to the invention is shown. An SEM image is captured of a portion of an exposed layer of the IC. The SEM image comprises information relating to circuit layout of the exposed layer and unexposed layers. In an embodiment, the information is filtered to extract circuit information therefrom. SIMS analysis of a same portion of the IC is used to distinguish between similar regions and to identify chemical composition of certain areas that require further analysis.

For example, doped areas are analysed to determine dopant type and concentration; conductors are analysed to determine composition; and so forth. Reverse engineering of layout information is substantially straightforward according to the present invention and in light of the prior art once geometric and chemical information is determined. As an example, all conductors within the IC are easily identified.

Application of such a method is particularly useful as reverse engineering becomes more automated and IC manufacturers search for methods of preventing automated reverse engineering. For example, using different compositions of material that appear similar when imaged but that perform different circuit functions prevents current automated reverse-engineering systems from properly analysing a circuit. According to the invention, because chemical information is analysed, these "hidden" components are also located and reverse engineered.

Figure 4:
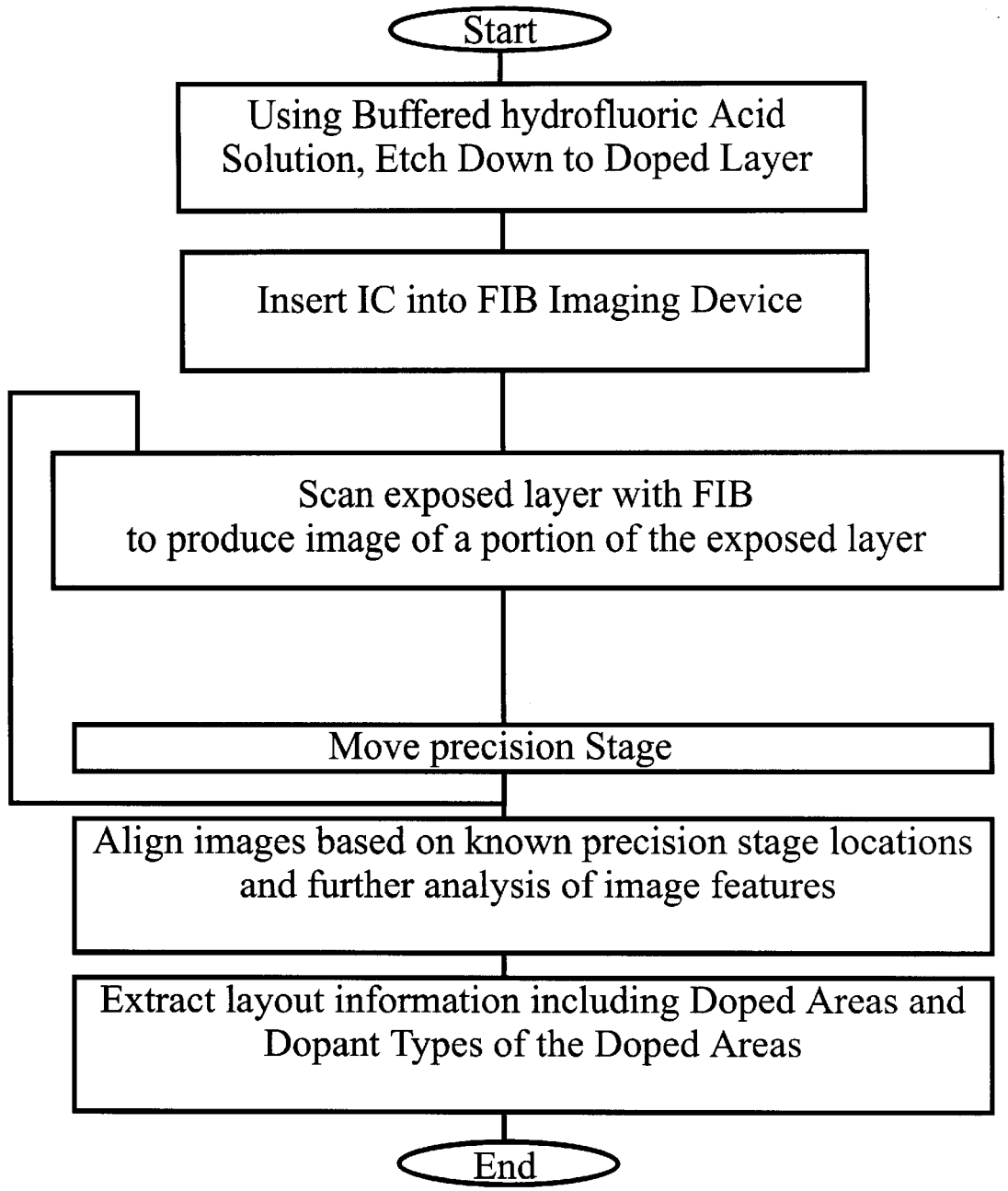

Referring to FIG. 4, a flow diagram of a broad embodiment of the present invention is shown. A doped substrate layer is exposed through etching of the integrated circuit. Preparation of integrated circuits by removing layers is well known. Commonly, a buffered hydrofluoric acid solution is used. A traditional buffered hydrofluoric acid solution is used to strip down the IC to its substrate layer. According to the process carried out during experimentation, extra hydrofluoric acid is added to the buffered hydrofluoric acid solution to increase etching rates. Alternatively, a regular buffered hydrofluoric acid solution is used. Sometimes metal is not removed by the solution and requires physical intervention; for example, brushing the metal with a soft cloth removes it and allows for continued etching. Conventionally, a buffered solution as disclosed requires about ten minutes to strip an IC down to its substrate. Preparation of ICs in this fashion is known for imaging integrated circuit layers.

Preferably for doped layers, FIB gas assisted etching is not used. This reduces any chance that ions used during the etching process implant within the doped layer, thereby effecting imaging results. Alternatively, the FIB is used to etch down to a doped layer and imaging results are analysed in light of the ion implantation. Since conventional etching is suggested, alignment between layers is lost since the IC is removed and replaced or is not a same IC as is used to image other layers. Preferably when a same IC is used for imaging each layer, alignment holes are etched into the IC to aid in interlayer alignment. Alternatively, bonding pads or other indicators of alignment between layers are used. Of course, human assisted alignment of layers is also possible.

The etched IC is inserted onto a stage where it is held in position by, for example, adhesive. Methods of retaining an IC stationary during imaging are well known in the art and any suitable method may be employed.

The exposed layer containing doped areas is then imaged using a FIB. A range of FIB imaging energies is applicable and can be easily determined through experimentation for providing best image results. The images thereby acquired contain significant variation depending on dopant types. Throughout this document and the claims that follow, dopant type is used to denote neutral or undoped areas, substantially low concentration dopants, $p^+$ dopants, $n^-$ dopants and other dopant types. The term dopant type does not refer to specific doping materials or substrate materials. Also of note is that a substrate layer that is doped in some areas is generally doped across the entire layer or a substantial part thereof and has areas of different doping existing within the doped layer. Semantically, an image shows a distinction between doped regions, rather than showing a distinction between doped regions and undoped regions. Alternatively, for polysilicon layers, doped regions are surrounded by undoped regions.

Using a scanning electron microscope, images are formed of an exposed surface of an integrated circuit and layers below the exposed surface. Because of the properties of a FIB system, only a surface of the integrated circuit is imaged. Therefore filtering of the image to remove background information is completely unnecessary. Image enhancement is performed to sharpen area borders between adjacent areas having differing dopant types or concentrations. A further step of image enhancement to remove noise and correct for image blur or deformation is also applied. Of course either of these steps may be omitted or alternatively, both steps may be performed as a single step.

A second stage of imaging comprising the step of chemical analysis of the doped substrate is performed. This provides additional information for use in imaging the doped layer(s).

The image acquired comprises pixels having different intensity levels or values, which are easily distinguishable as to dopant type. Areas are extracted from the enhanced image and associated with a dopant type for the area. The dopant type is determined based on imaging results and chemical analysis. This provides an accurate method of determining dopant concentrations, compositions and so forth. One method of extracting areas is using polygon extraction. Using polygon extraction, polygons are extracted representing each doped area. With each polygon geometry and location, a dopant type is stored associated with that polygon. The stored information is useful in extracting transistor information from integrated circuits.

Of course, a method such as that taught by Yu (U.S. Pat. No. 5,086,477) or by Lam (U.S. Pat. No. 5,694,481) may be applied to images of different locations on a same layer. Application of such a method results in a composite or mosaic image of a portion of a layer. Following the mosaicing of the above references or as is known in the arts of computer graphics, machine vision, and computer cartography, portions of different layers of an integrated circuit are imaged according to the invention, and a three-dimensional image of the layers registered one with another results. Because of the imaging of the doped layers and the chemical information, the resulting data is particularly useful for reverse engineering and integrated circuit analysis. Also, the resulting information provides a significant level of detail relating to the design and manufacture of the integrated circuit.

According to an embodiment of the invention, when a plurality of doped layers from a same IC are each imaged according to the invention and then vertically aligned, transistor layer layout information including dopant type is automatically extracted therefrom. Also in analysis of interconnects effected through connect lines on polysilicon layers, dopant types are determinable, whereas, prior art methods make identification of dopant types difficult—requiring significant skill to perform the task. Further, even with considerable skill reverse engineers often only manage to correctly determine dopant types of apparent doped regions most of the time. Errors in a determination of dopant type, result in flawed schematics. The schematics require further analysis, based on functionality, in order to accurately identify dopant types of doped areas. This is a significant drawback of the prior art.

According to a further embodiment of the invention, when all layers from a same IC are each imaged according to the invention and then vertically aligned, transistor layer layout information is automatically extracted and incorporated into schematics of the integrated circuit derived through a known circuit extraction method. Examples of known circuit extraction methods are taught by Yu in the U.S. Pat. No. 5,086,477. The presence of information relating to doped regions within the integrated circuit render circuit extraction more robust.

Circuit extraction is a process of extracting circuit information in the form of schematic information or layout information. Often, the information need not be complete for reverse engineering or circuit analysis. At other times, accuracy and completeness are required. According to the invention, more raw data is gathered from an integrated circuit allowing for more accurate extraction of circuit data therefrom. Alternatively, a same amount of information is extracted using less human intervention and skill.

Component information is a type of circuit information relating to individual components within a circuit. For example, a transistor location is component information as are transistor type, transistor size, transistor gate connections, dopant material, dopant concentration, capacitor location, etc.

For example, on the lowest doped layer—the substrate—a group of similarly doped regions is associated and on an adjacent layer, regions forming the rest of a component or a group of components is sought. The regions on the adjacent layer are generally proximate the doped regions on the substrate layer. More specifically, when two doped areas having n type dopant are located on the substrate layer in close proximity one to the other, then a gate likely exists in a location between the two areas on a layer above the substrate. Analysis of the adjacent layer, results in a located gate and identification of a transistor, or no located gate and, therefore, no component identification.

Traces are identified using a set of rules. These rules are easily understood by those of skill in the art. For example, a trace is formed of a conductive material and joins components. Components may be identified using a set of rules—for example npn or pnp doped areas. Alternatively, components are identified using templates. Because of variations in doped area size, shape and dopant concentrations, a rule-based approach is preferred. Those doped areas that are not associated with components are flagged for human review and identification or analysis. This reduces missed components or potential of omission of necessary doped regions in subsequent designs.

Even absent automated circuit component extraction, the method of imaging integrated circuits with chemical information extraction provides significant benefits. Heretofore, inference was used to extract information relating to chemical composition of traces, components, and doped regions of an integrated circuit. According to the invention, information is extractable from an IC image itself without intervention of highly skilled individuals.

Of course it is apparent to those of skill in the art that additional information relating to composition of integrated circuit layers results in improved automated image mosaicing and circuit extraction. This is a significant advantage of the present invention.

Also, it is apparent to those of skill in the art that the above methods are applicable to cross sectional imaging of an IC. The chemical information provides valuable information for automating the reverse engineering process.

Numerous other embodiments are envisioned without departing from the scope or spirit of the present invention.

What is claimed is:

1. A method of reverse engineering an integrated circuit comprising the steps of:

disposing the integrated circuit on a support for securing the integrated circuit in a fixed relation to the support; and iterating the following steps until a predetermined portion of an integrated circuit is imaged:

using an imaging system for providing a beam relatively movable to said support, imaging a portion of an outer surface of the integrated circuit by capturing a plurality of images of different locations on the integrated circuit, relative motion between the support and the beam occurring between image capture operations;

analysing chemical composition of a portion of the outer surface of the integrated circuit using a chemical analysis system different from the imaging system and relatively movable to said support; and, analyzing, with a processor, the plurality of captured images in dependence upon the analysed chemical information for determining information about a chemical composition of at least a portion of the integrated circuit.

2. A method of reverse engineering an integrated circuit as defined in claim 1 wherein the imaging system is a focused ion beam imaging system and the chemical analysis system is a secondary ion mass spectrometry system (SIMS).

3. A method of reverse engineering an integrated circuit as defined in claim 2 wherein the analysis of the chemical composition is performed for some of the imaged outer surface.

4. A method of reverse engineering an integrated circuit as defined in claim 3 wherein the analysed chemical composition is used to associate intensity ranges of pixels within the plurality of images with chemical compositions.

5. A method of reverse engineering an integrated circuit as defined in claim 3 wherein some of the associated intensity ranges overlap one another.

6. A method of reverse engineering an integrated circuit as defined in claim 1 comprising the step of marking the integrated circuit, the marks for providing image alignment information.

7. A method of reverse engineering an integrated circuit as defined in claim 6 wherein the marks are made using a scanning electron microscope system.

8. A method of reverse engineering an integrated circuit as defined in claim 6 wherein the marks are made using a focused ion beam system.

9. A method of reverse engineering an integrated circuit as defined in claim 1 wherein the step of analysing the plurality of captured images includes performing component recognition in dependence upon the analysed chemical information.

10. A method of reverse engineering an integrated circuit comprising the steps of:

disposing the integrated circuit on a support for securing the integrated circuit in a fixed relation to the support; and iterating the following steps until a predetermined portion of an integrated circuit is imaged:

using an imaging system for providing a beam relatively movable to said support, imaging a portion of an outer surface of the integrated circuit by capturing a plurality of images of different locations on the integrated circuit, relative motion between the support and the beam occurring between image capture operations;

using a chemical analysis system, different from the imaging system for analysing chemical composition of a portion of the outer surface of the integrated circuit; and, analysing, with a processor, the plurality of captured images in dependence upon the intensity values and associated chemical information for determining information about a chemical composition of at least a portion of the integrated circuit, by associating analysed chemical information and intensity values of pixels within the images at a same location as a location of the analysed chemical information.

11. A method of reverse engineering an integrated circuit as defined in claim 10 wherein the imaging system is a scanning electron microscope and the chemical analysis system is an EDX.

12. A method of reverse engineering an integrated circuit as defined in claim 10 wherein the step of analysing chemical composition is performed iteratively until a predetermined portion of an integrated circuit is analysed.

13. A method of reverse engineering an integrated circuit comprising the steps of:

disposing the integrated circuit on a support for securing the integrated circuit in a fixed relation to the support; and iterating the following steps until a predetermined portion of an integrated circuit is imaged:

using, an imaging system including a focused ion beam imaging device and a SIMS chemical analysis device relatively movable to said support imaging a portion of an outer surface of the integrated circuit by capturing a plurality of images of different locations on the integrated circuit with the imaging device and simultaneously analysing chemical information of the different locations using the SIMS device, relative motion between the support and the imaging system occurring between image capture operations; and analysing, with a processor, the plurality of captured images in dependence upon the analysed chemical information for determining information about a chemical composition of at least a portion of the integrated circuit.

* * * * *